US008795182B2

(12) United States Patent
Shafir et al.

(10) Patent No.: US 8,795,182 B2
(45) Date of Patent: Aug. 5, 2014

(54) SWITCH FOR APERTURE CONTROL IN MEDICAL DIAGNOSTIC ULTRASOUND IMAGING

(75) Inventors: Haim Shafir, Cupertino, CA (US); Christopher M. Daft, Dublin, CA (US); Paul A. Wagner, San Carlos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 520 days.

(21) Appl. No.: 12/780,795

(22) Filed: May 14, 2010

(65) Prior Publication Data

US 2011/0021920 A1 Jan. 27, 2011

Related U.S. Application Data

(60) Provisional application No. 61/227,639, filed on Jul. 22, 2009.

(51) Int. Cl.
| | |
|---|---|
| A61B 8/14 | (2006.01) |
| G01N 29/24 | (2006.01) |
| G01N 29/26 | (2006.01) |
| G01N 29/06 | (2006.01) |
| G01S 15/89 | (2006.01) |
| G01S 7/52 | (2006.01) |
| A61B 8/00 | (2006.01) |

(52) U.S. Cl.
CPC .......... *G01N 29/0654* (2013.01); *G01N 29/245* (2013.01); *G01N 29/262* (2013.01); *G01S 15/8925* (2013.01); *G01S 7/52085* (2013.01); *G01S 15/8927* (2013.01); *A61B 8/54* (2013.01)

USPC ............ 600/459; 600/447; 327/12; 327/100; 327/124

(58) Field of Classification Search
USPC ......... 600/407, 437, 441, 443, 446, 447, 455, 600/459; 327/12, 18, 49, 64, 97, 107, 118, 327/203, 207, 223
See application file for complete search history.

(56) References Cited

U.S. PATENT DOCUMENTS

| | | | | |
|---|---|---|---|---|
| 6,676,602 | B1 * | 1/2004 | Barnes et al. | 600/443 |
| 6,836,159 | B2 * | 12/2004 | Wodnicki | 327/100 |
| 7,313,053 | B2 * | 12/2007 | Wodnicki | 367/153 |
| 7,353,056 | B2 * | 4/2008 | Hazard et al. | 600/407 |
| 2002/0135415 | A1 * | 9/2002 | Dufort | 327/333 |
| 2004/0122321 | A1 * | 6/2004 | Alexandru | 600/459 |
| 2005/0061085 | A1 * | 3/2005 | Jespersen | 73/861.27 |
| 2005/0148879 | A1 * | 7/2005 | Ramamurthy et al. | 600/459 |
| 2005/0267369 | A1 * | 12/2005 | Lazenby et al. | 600/447 |
| 2007/0016026 | A1 * | 1/2007 | Thomenius et al. | 600/437 |

OTHER PUBLICATIONS

Platt, John C., *Optimal Filtering for Patterned Displays*, IEEE Signal Processing Letters, vol. 7, No. 7, Jul. 2000, pp. 179-181.

* cited by examiner

*Primary Examiner* — Unsu Jung
*Assistant Examiner* — Michael N Fisher

(57) ABSTRACT

Switching is provided in a transducer array of medical diagnostic ultrasound imaging. The switching controls the formation of macro elements or aperture for scanning a plane or volume. The switches are implemented with one or more transistors. The control causes the gates of the transistor to float during the "on" connection. While on, the switch connects, allowing ultrasound signals to pass through the switch.

20 Claims, 8 Drawing Sheets

SWITCH FOR APERTURE CONTROL IN MEDICAL DIAGNOSTIC ULTRASOUND IMAGING

RELATED APPLICATIONS

The present patent document claims the benefit of the filing date under 35 U.S.C. §119(e) of Provisional U.S. Patent Application Ser. No. 61/227,639, filed Jul. 22, 2009, which is hereby incorporated by reference.

BACKGROUND

The present embodiments relate to ultrasound transducers. In particular, the present embodiments relate to a reconfigurable transducer array.

One-dimensional transducers are used to scan a plane with electronic steering. For scanning a volume, a two-dimensional transducer may be used. However, the number of beamforming channels greatly increases for scanning with a two-dimensional transducer. Many ultrasound imaging systems do not have sufficient channels. An alternative is a mechanically rotated one-dimensional transducer (i.e., a wobbler). However, the mechanical motion may be insufficiently rapid for real-time volume scanning.

A multi-dimensional transducer array may be used with electronic switching to both provide for volume scanning and a fewer number of required beamformer channels. U.S. Pat. No. 6,676,602 describes such embodiments. For example, an electronically rotated array is an array of elements where the aperture used during scanning is electronically controlled. Switches connect different elements to different beamformer channels, allowing rotation of the aperture for sequential scanning. For example, a one-dimensional aperture is rotated electronically on the face of a two-dimensional transducer array. By controlling the configuration of the switches, the one-dimensional array may be oriented to any rotational angle. Within a given aperture, the defined one-dimensional array may steer scan lines. For volume scanning, the volume is sampled by collecting a series of azimuth-spaced beam groups at each rotation angle.

The switching to allow beamformation in real-time volume scanning may require high performance switches. For interconnecting a plurality of elements, the switches should have low "on" resistance. Isolation in the "off" state helps with beam formation. The size of the switch is also important since the switches may be placed within a small probe for operating with thousands of acoustic elements. Conventional switching approaches suffer from issues such as 1/f noise, crosstalk, impractical DC power, die size, or parasitic capacitance.

BRIEF SUMMARY

The present invention is defined by the following claims, and nothing in this section should be taken as a limitation on those claims. By way of introduction, the preferred embodiments described below include methods and systems for switching in a transducer array of medical diagnostic ultrasound imaging. The switching forms macro elements, which in turn, form apertures for scanning. The switches are implemented with one or more transistors. The gates of the transistors float during the "on" connection. While on, the switch connects, allowing ultrasound signals to pass through the switch.

In a first aspect, a transducer array is provided for medical diagnostic ultrasound imaging. A plurality of elements is provided. A plurality of channel lines is connected to a beamformer. A plurality of switches is arranged to interconnect sub-sets of the elements together into macro elements and to interconnect the macro elements with respective channel lines. At least a first one of the switches comprises at least two pass transistors and a controller arranged to float gates of the at least two pass transistors when the switch is on.

In a second aspect, a switch is provided for interconnecting elements of an electronically configurable transducer array in medical diagnostic imaging. A first connection is provided with a first switch or a first beamformer channel. A second connection is provided with a second switch or a first transducer. A first MOSFET has a gate, a source and a drain. A first control transistor connects with the gate. The first control transistor is operable to float the gate when the first MOSFET is on where electrical signals for beamformation pass through the switch when the first MOSFET is on and do not pass through when the first MOSFET is off.

In a third aspect, a method is provided for connecting elements together in medical diagnostic ultrasound imaging. A switch connects a first transducer element to a second transducer element. A gate of the switch is disconnected during the connection of the first and second transducer elements. Imaging is performed with the first and second transducer elements as an electrically common macro element during the connecting. The first transducer element is disconnected from the second transducer element with the switch. The gate of the switch connects to ground during the disconnecting.

Any one or combinations of any two or more of the aspects discussed above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Electronically rotatable one-dimensional ultrasound arrays may provide a simplified and low cost real-time three-dimensional volume acquisition suitable for cardiac or other imaging. Fewer beamforming channels may be needed than scanning with a fully sampled two-dimensional array.

A switch matrix allows the imaging system to operate with macro elements. For example, a 2D array of $N^2$ elements may be connected through $O(N)$ analog wires to the imager with minimal power consumption at the transducer and simple digital control. This switching approach may be used where autonomous-channel matrix arrays are too costly.

To fit underneath the array in one embodiment, the switch structure area is smaller than acoustic element size. Other locations for the switching are provided in other embodiments. Integrated circuit process may provide practical combinations of "on" resistance and "off" parasitic capacitance. For example, an integrated circuit incorporates a bi-directional high-voltage switch with two pass MOSFETs. A control mechanism provides for the MOSFETs' gates to float during the imaging time.

By having a small area, a switch may be used in highly constrained applications, such as transesophageal endoscopy (TEE), as well as other volume imaging scenarios. A switch fabric is provided for a TEE configurable cMUT or other array. The total power dissipation may be low, such as less than a watt, even where many (e.g., 2500) switch cells are provided, each in a 200 micron hexagon. A bidirectional switch with a resistance of 300 ohm and capacitance of about 0.5 pF may be provided to interconnect the matrix of acoustic elements. Other design characteristics may be used.

Figure 1:
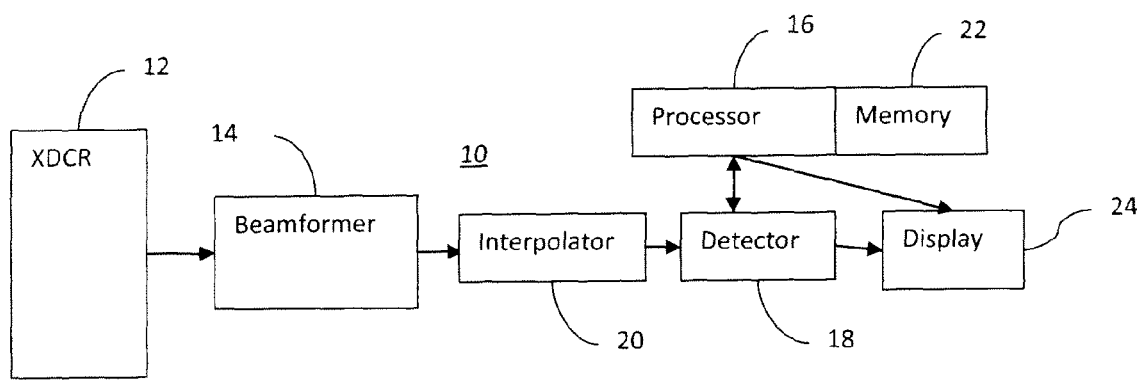
FIG. 1 is a block diagram of one embodiment of a system for scanning with ultrasound.

FIG. 1 shows a system 10 for scanning with a multi-dimensional transducer for medical diagnostic ultrasound imaging. The system 10 includes a transducer probe 12, a beamformer 14, a processor 16, a detector 18, an interpolator 20, a memory 22, and a display 24. Additional, different, or fewer components may be provided. For example, the system 10 includes a user interface. In one embodiment, the system 10 is a medical diagnostic ultrasound imaging system. In other embodiments, the processor 16 and/or memory 22 are part of a workstation or computer different or separate from an ultrasound imaging system. The workstation is adjacent to or remote from the ultrasound imaging system.

In some embodiments, the transducer probe 12 is provided without other components. The transducer probe 12 is a transducer array for medical diagnostic ultrasound imaging. The transducer probe 12 may be used with the system of FIG. 1 or a different system. The transducer probe 12 is a planar array, a curved array, a two-dimensional array, a radial array, an annular array, or other multidimensional array of transducer elements. For example, the transducer probe 12 is a multi- or two-dimensional array.

Figure 2:
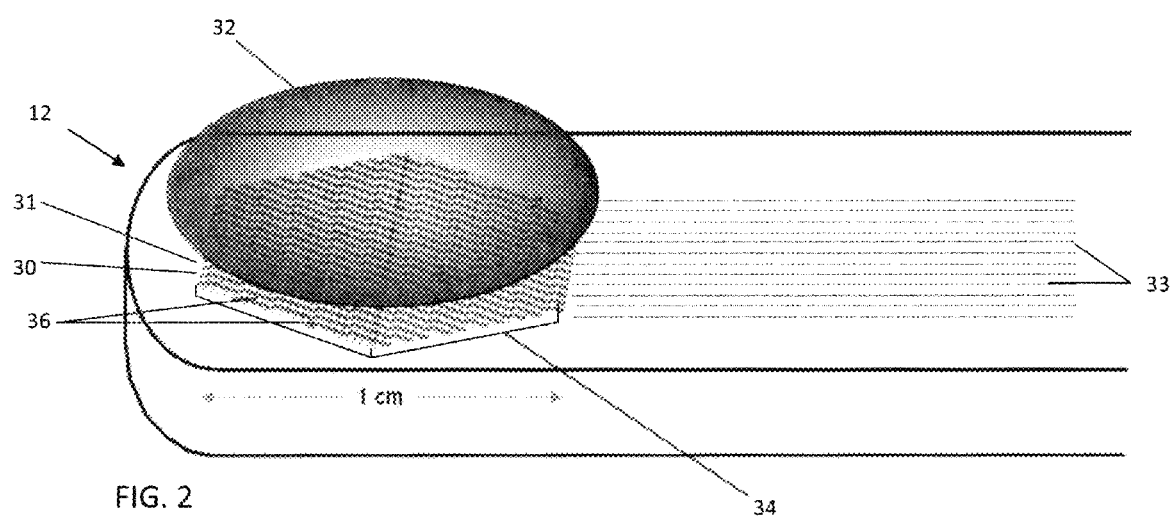
FIG. 2 illustrates an example transducer probe.

In one embodiment, the transducer probe 12 is adapted for use external to the patient, such as including a hand held housing or a housing for mounting to an external structure. In another embodiment, the transducer probe 12 is adapted for use within the patient, such as a transesophageal probe, an endocavity probe or other probe for scanning while positioned within or in the interior of a patient. For example, the transducer is used as an electrically rotatable 1D transesophageal (TEE) probe as represented by FIG. 2. A 1 cm hex array with about 2500 elements is provided, where the array is used with about 48 beamformer channels and associated coaxial cables and a bias line (in the case of a capacitive transducer or cMUT). Other sizes, numbers of elements, and/or numbers of channels may be provided.

Electronic rotation may be performed at a higher speed than mechanical rotation. For example, the one-dimensional array aperture may be electronically rotated to any angle in microseconds or nanoseconds, enabling real-time volumetric imaging while minimizing cable count between the system and the transducer probe 12.

The multi-dimensional transducer probe 12 is an array 31 of an N by M arrangement of acoustic elements 36, where N and M are both greater than one. The array sampling pattern or relative placement of one acoustic element 36 to another acoustic element 36 is based on any sampling method, such as a triangular grid, rectangular grid, hexagonal grid, irregular grid, or random grid. Various spacing may be provided, such as ½ or one wavelength spacing between the centers of adjacent elements. In one embodiment, the grid has about ⅓ or ¼ wavelength spacing. The face or surface of the entire array 31 is square, rectangular, triangular, hexagonal, irregular, or other shape. Any of various possible multi-dimensional arrangements of acoustic elements 36 may be used for the multi-dimensional transducer probe 12. The array 31 is either flat or includes concave or convex curvature.

Figure 3:
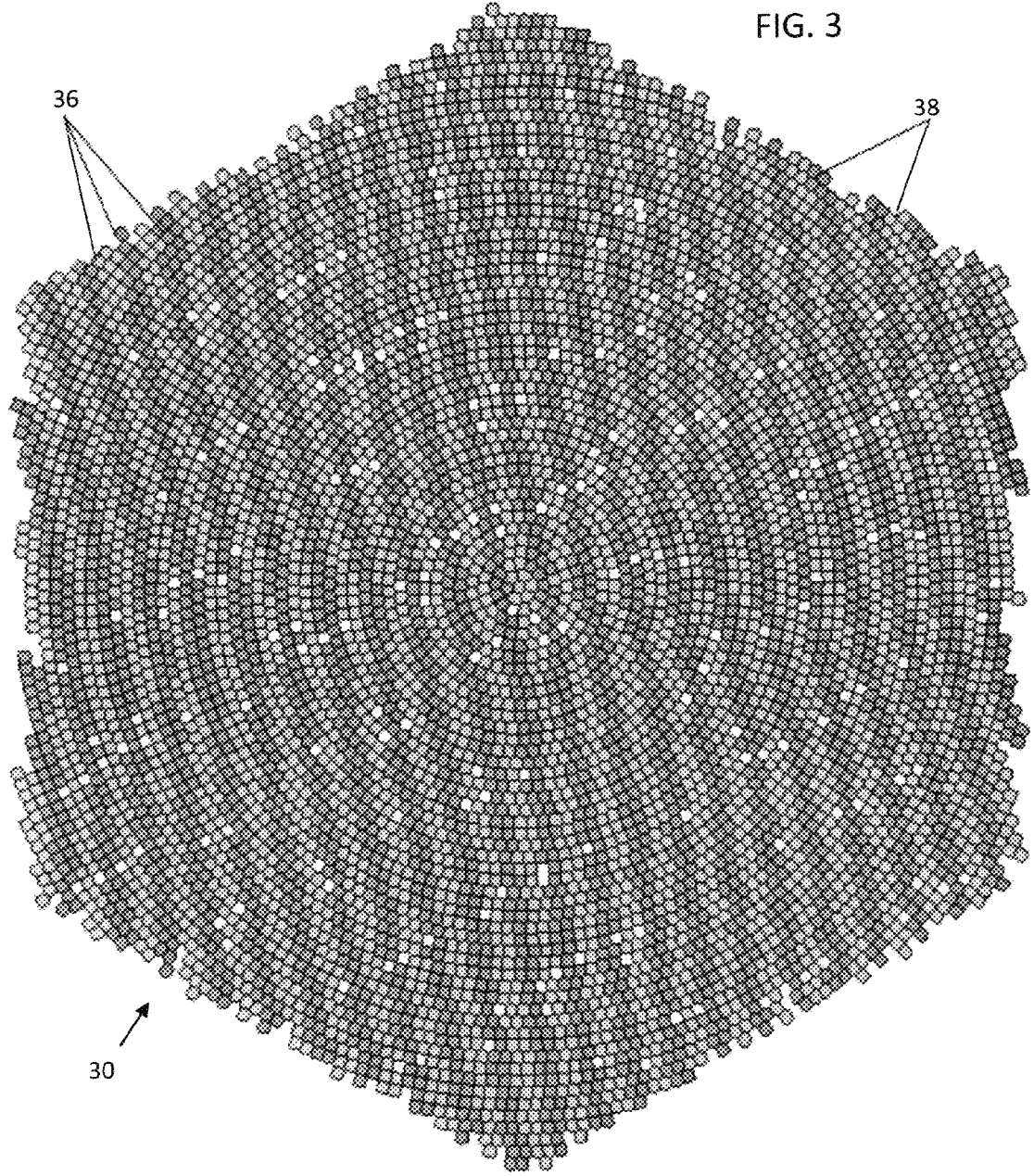
FIG. 3 is a top view of one embodiment of the distribution of acoustic elements with interconnected elements forming macro elements in a one-dimensional array.

As represented in the example of FIG. 3, an electronically rotated phased array may be implemented using the multi-dimensional array 31 of acoustic elements 36 and an array of semiconductor or MEMS switches. The switches electronically connect elements into a phased array of macro elements 38. The macro elements 38 are individual elements 36 of the array 31 or are formed by interconnection of a plurality of elements 36. For focal point locations over most of the depth of the beam, the macro elements 38 may be a plurality of parallel, substantially straight lines. Where response time of switches within the electronically configurable array is sufficient, the interconnection of acoustic elements 36 to correspond with constant delay contours dynamically changed during the reception of a beam, such as changing from concentric circular, to elliptical, and to substantially straight macro elements 38. Also, the macro elements 38 may represent a contour derived from and used for multiple focal points without any dynamic changes for a given beam or scan plane. Alternatively or additionally, the macro elements 38 are grouped, such as in rows, corresponding to different focal points. Different rows or all of the rows are used for different focal points. The macro elements 38 are aligned in an image plane direction.

By reconfiguring the macro elements 38, the image plane direction is rotated for scanning the three-dimensional volume. A set of rotated two-dimensional image planes are acquired as a three-dimensional data set. The rotated phased array of macro elements 38 may be either a 1D, 1.75D or other phased array. In alternative embodiments, macro elements 38 are not used. Instead, a 1D, 1.75D or other array is formed from elements of the multi-dimensional transducer without combining elements into macro elements 38.

Referring again to FIG. 2, the transducer probe 12 includes an acoustic element layer 30, a lens 32, and a switch layer 34 for scanning using the electronically established aperture. Additional, different or fewer components may be provided. For example and as shown in FIG. 2, a housing may be provided.

The acoustic element layer 30 is planar, curved, concave, convex or other surface shape. The acoustic element layer 30 includes a plurality of acoustic elements 36. The acoustic element layer 30 is a single layer of acoustic elements 36 or may include multiple layers of acoustic elements 36. The acoustic elements 36 are transducer elements for transducing between electrical and acoustic energies.

The acoustic elements 36 of the transducer probe 12 are lead zirconate titanate (PZT) piezoelectric transduction material, ferroelectric relaxor or PVDF materials, capacitive membrane ultrasonic transducer (cMUT) materials, micro-machined membranes or beams, microelectromechanical devices, other piezoelectric material, or other means for acoustic-to-electric and/or electric-to-acoustic transduction. For example, the acoustic elements 36 are cMUT or micromachined structures, such as at least one flexible membrane suspended over a gap with electrodes on each side of the gap for transducing between acoustic and electrical energies. Each acoustic element 36 is formed from one or more, such as 4-8, tens or other numbers of membranes and gaps (i.e., "drums" or cMUT cells). The electrodes of each of the membranes and gaps for a given element 36 are connected in common to form the single acoustic element 36.

All of the acoustic elements 36 comprise a same type of material, but multiple types of acoustic transducer materials may be used for different acoustic elements 36. The acoustic elements 36 have one of various possible shapes, such as triangular, rectangular, square, polygonal, hexagonal, circular, irregular, or any combination of shapes on the face of the acoustic element 36 (i.e., portion of the element 36 placed adjacent a volume to be scanned).

The transducer probe 12 converts between electrical signals and acoustic energy for scanning a region of the patient's body. The region of the body scanned is a function of the type of transducer array 31, position of the transducer probe 12 relative to the patient, and the underlying switch setting. At a given switch configuration, a linear aperture may scan a rectangular or square, planar region of the body. As another example, a curved linear aperture may scan a pie shaped region of the body. Scans conforming to other geometrical regions or shapes within the body may be used, such as Vector™ scans. The scans are of a two-dimensional plane, such as scanning at different azimuth angles relative to the aperture. Different planes or different segments of a plane may be scanned by moving an aperture of the transducer probe 12. The aperture may be electronically moved (e.g., rotated relative to the face of the array 31) without movement of the transducer probe 12. A volume is scanned. The volume is scanned by electronic steering and switching.

In one embodiment, the acoustic elements 36 are aperiodic across a face of the transducer array 31. FIG. 3 shows aperiodic distribution of the acoustic elements 36 in a radially symmetric pattern. Radial symmetry may not be provided in other embodiments. The acoustic elements 36 are generally positioned in a periodic or regular grid. One or more of the elements 36, such as a majority or all of the elements 36, are shifted in different directions and/or by different amounts to create an aperiodic pattern. The shifts are by less than a pitch of the grid, such as being 10-100 microns where each acoustic element is about 0.2 mm in diameter. "About" accounts for manufacturing tolerance or other differences within 10%. Other sizes of elements 36 and/or shifts could be used. The aperiodic arrangement of the acoustic elements 36 leaves gaps between the elements. Alternatively, the elements are sized differently to account of the shifts. Aperiodic shifts may be provided by a partially randomized radial layout format or other shift distribution.

Where the acoustic elements 36 are cMUTs, the array 30 is formed using lithography or other semiconductor process. The pattern of the acoustic elements 36, such as the aperiodic pattern, is designed and used for forming the array 31.

In alternative embodiments, the acoustic elements 36 are patterned periodically or on the base periodic grid. The acoustic elements 36 may have a same or different periodicity as the switches of the switch layer. For example, periodic distribution of the acoustic elements 36 is provided, but with a different pitch than of the switches used for forming the apertures.

The acoustic layer 30 is stacked along a depth dimension or generally orthogonally to the face of the acoustic layer 30 with the switch layer 34. "Generally" accounts for curvature of the acoustic layer 30 and/or the switch layer 34 or manufacturing tolerance. In one embodiment, the stacking is conceptual as the layers are formed in the same silicon substrate. In other embodiments, the layers 30, 34 are formed on different structures and are literally stacked. None, one or more other layers of material or structure may be positioned in between the acoustic element layer 30 and the switch layer 34.

The switch layer 34 connects the acoustic elements 36 into macro elements 38 and connects the macro elements 38 to the beamformer channels 33. As represented in FIG. 2, the beamformer channels 33 are separate traces and/or coaxial cables for beamformation. Any number of beamformer channels 33 may be provided, such as tens or hundreds (e.g., 64, 128, or 356). None, one or more other lines may be provided, such as for control signals, bias (for cMUTs), or communications.

The channels 33 connect to or are connectable with the beamformer 14. For example, the transducer probe 12 may be detached and reattached to the imaging system. When attached, the channels 33 from the transducer probe 12 connect with the channels of the beamformer 14. Permanent connection may be provided.

The switch layer 34 connects the acoustic elements 36 to the channels 33. The switch layer 34 is planar, curved, concave, convex or other surface shape. The switch layer 34 is a single layer of switches or may include multiple layers of switches.

The switch layer 34 includes a plurality of switches. The switches are arranged to interconnect sub-sets of the elements 36 together into the macro elements 38 and to interconnect the macro elements 38 with respective channel lines 33. The switch layer 34 is part of an electronically configurable transducer array 31 in medical diagnostic imaging.

Figure 5:
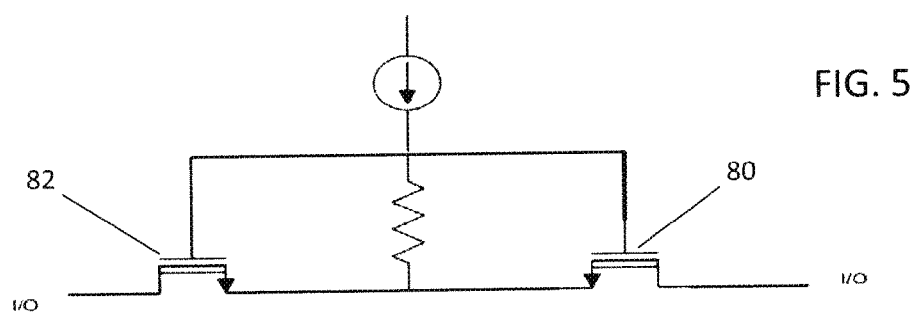
FIG. 5 is a circuit diagram of a switch according to one embodiment.

In one embodiment, the switches are transistors with gates allowed to float (disconnected from a source or ground) when the switch is "on" (i.e., closed to connect). The capacitance between the source and gate is charged to a sufficient level that the transistors remain on even though the gates are isolated from the rest of the circuit. FIG. 5 shows one embodiment of a switch. This switch provides for a floating gate of the two MOSFETs. The switch is controlled by a voltage source hanging on the high rail. The current source is protected by a high voltage (HV) cascade. To turn the switch "on," a DC current flows through the resistor into the source.

Figure 6:
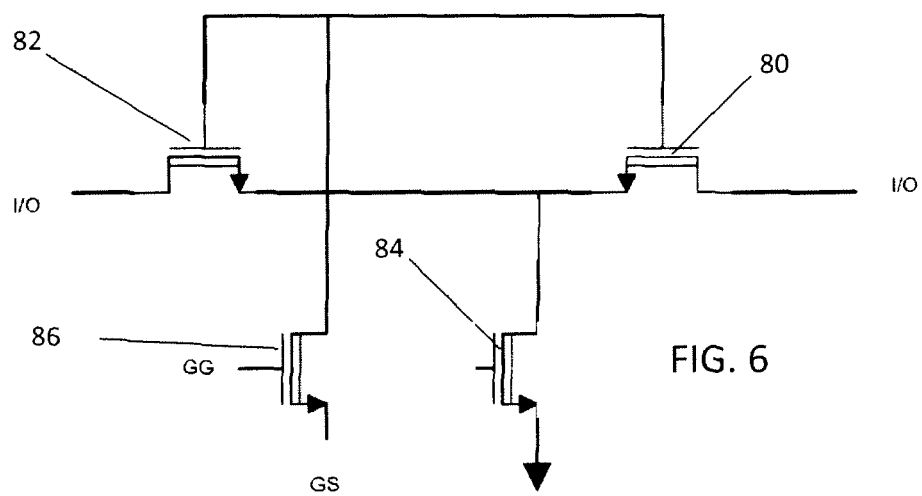
FIG. 6 is a circuit diagram of a switch according to another embodiment.

FIG. 6 shows another embodiment of the switch. High voltage transistors 80, 82 and control transistors 84, 86 are provided. The switch is a bi-directional high-voltage switch with two pass transistors 80, 82, and a control for the transistors 80, 82 where the gates float during imaging.

The switch has a first I/O connection with another switch, a beamformer channel 33, or an acoustic element 36 (transducer). The other I/O connects with another switch, or an acoustic element 36. The connections configure the switch to interconnect different sub-sets of elements 36 into different macro-elements 38 multiple times within a second. By turning the switch on or off, the switch connects (closed switch) or disconnects (open switch) one I/O from the other I/O.

In one embodiment, there are two pass transistors 80, 82, but one, three, or more may be provided. Any transistor may be used, such as large switch 50 v or greater DMOS MOSFETs. High voltage signals are unipolar, varying from zero to 50 volts through the switch. Other embodiments may allow for bipolar signals.

In the arrangement shown in FIG. 6, the pass transistors 80, 82 each have a gate, a source and a drain. The sources of the pass transistors 80, 82 connect together. The drain of one pass transistor 82 connects to the I/O (e.g., connects to the acoustic element 36 or another switch), and the drain of the other pass transistor 80 connects to the other I/O (e.g., connects to another switch or a channel 33). The gates of the pass transistors 80, 82 connect together. Other connections may be used.

One or more control transistors are provided, such as two control transistors 84, 86. The control transistors 84, 86 form a controller arranged to float gates of the pass transistors 80, 82 when the switch is "on." Three or more control transistors or other control circuits may be used. In one embodiment, the control transistors 84, 86 are high voltage DMOS devices, such as MOSFETs, to control the switch.

The control transistors 84, 86 operate in response to logic supplies GG, GS, and SG. The logic supplies each provide either a 3 v or ground signal. Switch control inverter supplies may be 3-4 volts and ground. During switch programming, the high voltage through the pass transistors 80, 82 is maintained at zero.

One of the control transistors 86 has a drain connected with gates of the two pass transistors 80, 82, a gate connected with the GG control signal source, and a source connected with the GS control signal source. The control transistor 86 floats the gates of the pass transistors 80, 82 when the pass transistor 82 is "on." The electrical signals for beamformation pass through the switch when the pass transistors 80, 82 are "on" and do not pass through when the pass transistors 80, 82 are "off." The electrical signals are high voltage signals ranging from zero to 50 volts in a unipolar waveform with a low voltage rest at zero volts.

The other control transistor 84 has a drain connected with sources of the two pass transistors 80, 82, a source connected with ground, and a gate connected with the SG control signal source. This control transistor 84 maintains the switch "off" while the other control transistor 86 may be used to charge the gates in a transition to "on."

The switch has at least three states, but more or fewer states may be provided. In a first state, the switch is "on," connecting the I/O together. In a second state, the switch is "off," disconnecting the I/O from each other. In a third state, the switch is transitioning to "on," such as by charging the gates of the pass transistors 80, 82.

For the switch to be off, the controller connects the gates and sources of the pass transistors 80, 82 to ground. The control signals SG and GG are at DC 3 volts, and the control signal GS is pulled to ground. This turns the control transistors 84, 86 on, connecting the sources and gates of the pass transistors 80, 82 to ground through the control transistors 84, 86. The source and gate of the switch DMOS are pulled to ground and the switch is off.

For the transition state, the controller charges the gates of the pass transistors 80, 82 during a transition to "on" while maintaining the sources at ground. The control transistor 84 maintains the connection of the sources of the pass transistors to ground (SG remains at 3 volts). The other control transistor 86 charges the gates of the pass transistors 80, 82 through a body diode. A common or same voltage (e.g., 3 volts) is applied to the gate and source of the control transistor 86. For example, both GS and GG are pulsed to 3 volt for 100 ns, and then the gates are connected back to ground. By applying the same or similar voltage, the control transistor 86 is off. The gates of the pass transistors 80, 82 are charged via the source-to-drain diode of the control transistor 86. The source is then pulled to ground.

The three gates driving the control transistors 84, 86 are 5v CMOS in an isolated tub. This enables compensation for the diode drop and charging the DMOS switch gate to full 3.3 volt by raising the 5v CMOS supply to 4 volts. Node GG turns off before GS is pulled back to ground to prevent gate discharge.

For turning the switch completely on, the controller disconnects the sources from ground. The control transistor 86 allows the gates of the pass transistors 80, 82 to float by having a common voltage applied at the gate and source of the control transistor 86. The ground connection to the sources of the pass transistors 80, 82 is turned off by control transistor 84. After the gate is charged in the transition state, the control transistor 84 is turned off. The switch is on and can float on the high voltage signal.

A plurality of the switches is operable to interconnect the acoustic elements 36 into a plurality of macro elements 38 (see FIG. 3). Most or all of the macro elements 38 include at least two electrically connected acoustic elements 36. For example, the acoustic elements 36 are connected in a substantially straight line, chevron patterns or in curving patterns in at least two dimensions (i.e. across the face of the transducer array 31). For operation as a phased array, each macro element 38 is continuous across the face of the two-dimensional array 31 or a defined aperture.

In one embodiment, the switches may be integrated directly under the acoustic elements 36 to minimize interconnect parasitic capacitance. The switches are high voltage (e.g., tens or hundreds of volts), small footprint switches. The switches are fabricated using semiconductor fabrication processes allowing a large number of devices to be fabricated on a single silicon or other semiconductor chip, but two or more chips may also be used. It is possible to include electronic circuitry and switches on the same silicon chip, allowing the switch control circuitry to be integrated with the switches on the same chip. The switches and array may be provided in a probe housing, providing a small, low cost, high yield three-dimensional imaging transducer using low power consumption, resulting in better transducer thermal efficiency. Minimal or no changes are needed in conventional imaging system channel hardware.

Figure 4:
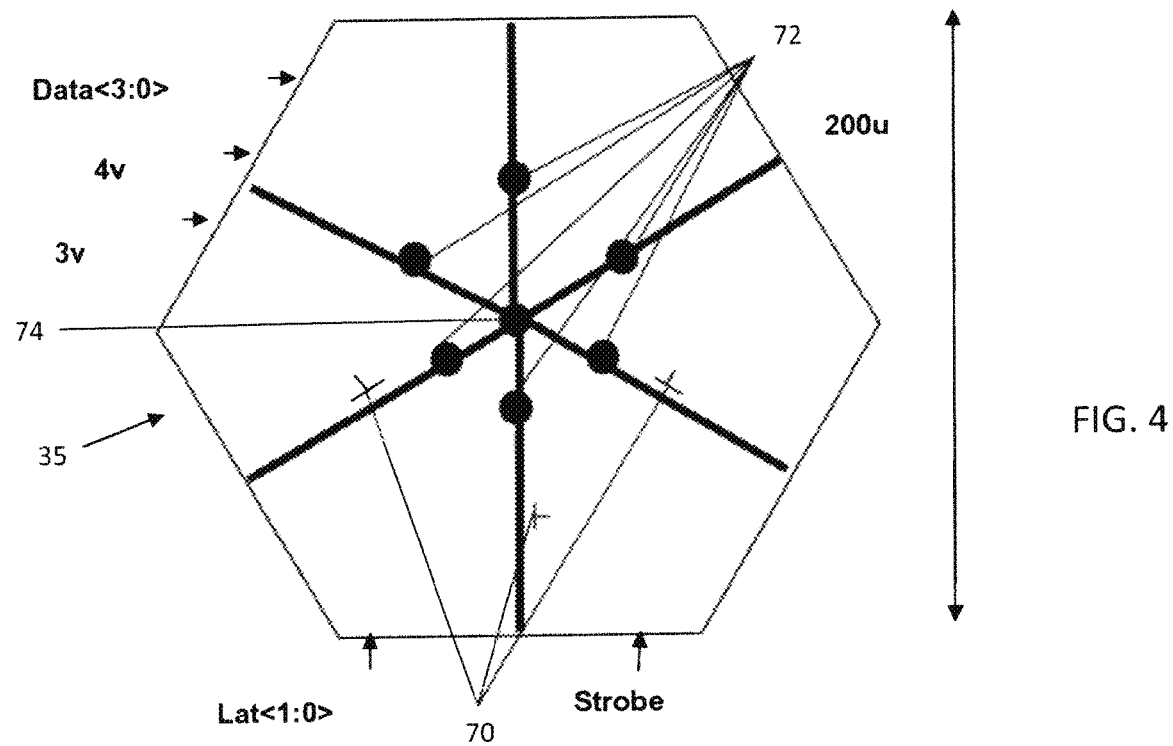
FIG. 4 is an illustration of an example switch cell for interconnecting acoustic elements.

FIG. 4 shows a switch cell 35 of the switch layer 34. The switches may be formed into a plurality of switch cells 35. The switch cells 35 are distributed in the switch layer 34 in a regular hexagonal, rectangular, triangular, or other grid. The distribution is periodic, but may be randomized or aperiodic. The distribution is the same or different grid pattern, lateral extent, and number as the acoustic elements 36 of the acoustic layer 30.

Each switch cell 35 includes a plurality of switches. For example, the switch cell 35 includes lateral (trunk) switches 70, vertical (spoke) switches 72, and/or an entry switch 74. The switches 70, 72, and 74 are for connecting beamformer channels 33 with acoustic elements 36 and interconnecting acoustic elements 36. Other arrangements may be provided.

Figure 7:
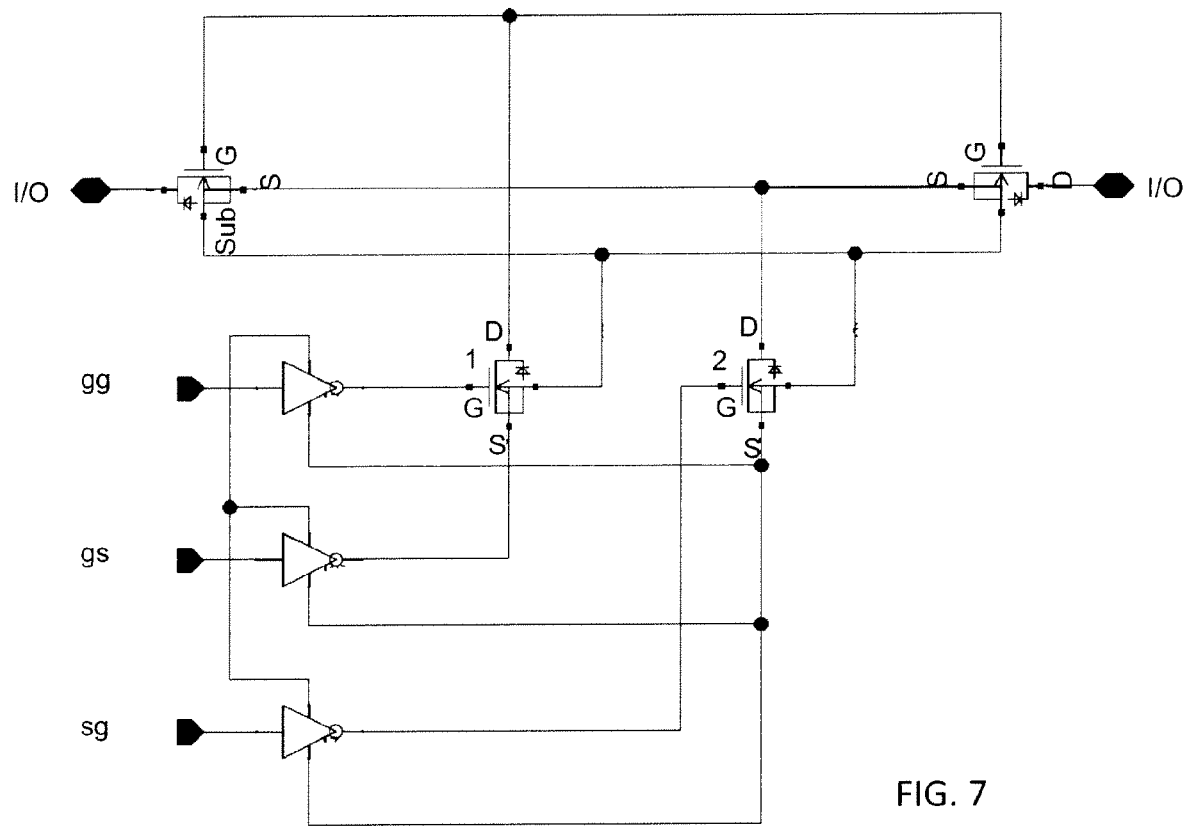
FIG. 7 is a circuit diagram of one example of the switch of FIG. 6.

One or more lateral switches 70 are provided for connecting to adjacent switch cells 35. FIG. 7 shows an example of the switch in FIG. 6. As a lateral switch 70, the gate width may be 160u, but larger or small sizes may be used. The "on" resistance is less for larger size.

In a hexagonal grid, three lateral switches 70 may be provided in each switch cell 35 for connecting with three of the six adjacent switch cells 35. By arranging the lateral switches 70 in each switch cell 35, different interconnections between a given switch cell 35 and the six adjacent switch cells 35 may be provided.

Each switch cell 35 includes one or more (e.g., at least two) vertical switches 72 for connecting the switch cell 35 to a respective one or more acoustic elements 36. Vertical and lateral are used to describe the connection rather than the layout or orientation of the switch. Any layout or orientation may be used, such as the lateral switches surrounded by vertical switches, all formed in a same plane.

As a vertical switch 72, the gate width may be 24u, but larger or small sizes may be used. The "on" resistance is greater for this smaller size as compared to the lateral switch 70. The vertical switches 72 are designed to have a higher "on" resistance (Ron) than the lateral switches 70. Low Ron switches occupy a larger area. The low Ron lateral switches 70 feed current into the macro element chain, while high Ron, smaller area vertical switches 72 redistribute reduced amounts of current from the electronic cell matrix to the acoustic cell matrix 2D elements. The vertical switches 72 may have higher Ron, to reduce the area. In one embodiment, all of the vertical switches 72 have the same Ron characteristic within manufacturing tolerance. In other embodiments, one or more of the vertical switches 72 may have even higher Ron than other vertical switches. For example, primary switch cell to acoustic element connections have a lower Ron vertical switch 72. Secondary vertical switches 72 connect with secondary acoustic elements (e.g., adjacent). The higher Ron routes less of the electrical energy to that element, causing contribution but to a lesser extent in beamformation. By planning the distribution of primary and secondary vertical switches 72, such as one acoustic element 36 being connected through a primary vertical switch 72 to one switch cell 35 and being connected to an adjacent switch cell 35 through a secondary vertical switch 72, most or all of the acoustic elements 36 may be used as "full strength" elements or "lesser" strength elements.

In one embodiment, six or seven vertical switches 72 are provided in each switch cell 35. Each vertical switch connects to one of six or seven adjacent acoustic elements 36. The adjacent acoustic elements 36 are adjacent to each other. A given acoustic element 36 may connect to one or more switch cells 35, but the switches are operated to avoid connection of different switch cells 35 to a same acoustic element 36 at a same time unless sharing a same beamformer channel.

A sub-set of the switch cells 35 include entry switches 74. The entry switches connect the beamformer channels 33 with macro elements 38. In one embodiment, the entry switches 74 are in switch cells 35 arranged along a geometric diagonal (primary) or three straight lines of the hexagonal grid. Other arrangements of entry switches may be provided. The entry switch 74 is the switch of FIG. 7, but other switches may be used. The switch cells 35 with an entry switch 74 may have fewer lateral switches 70, such as having two lateral switches 70 instead of three. Alternatively, the same number of lateral switches 70 is provided for cells 35 with and without entry switches 74.

Figure 8:
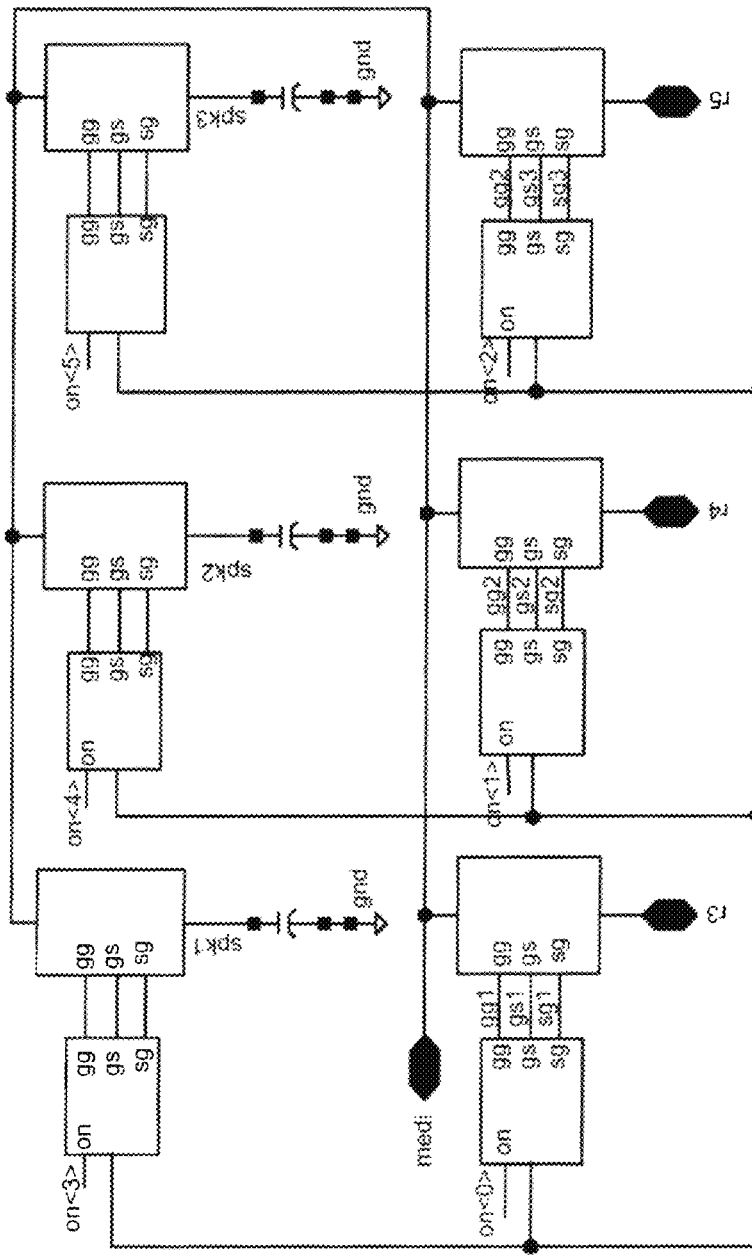
FIG. 8 is a block diagram of one embodiment of a switch cell using the switch circuit of FIG. 6.
Figure 9:
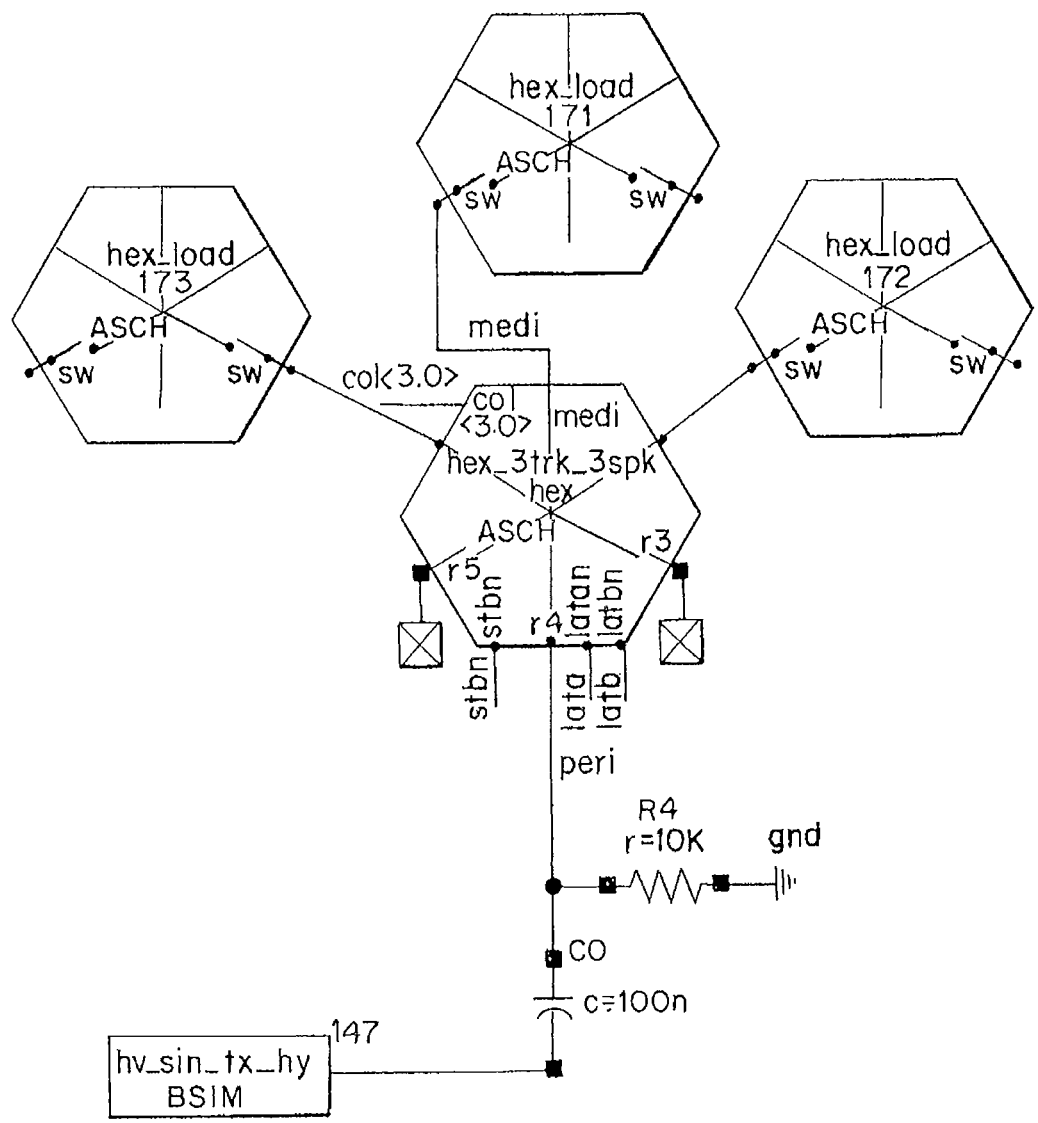
FIG. 9 is an example sub-set of switch cells of FIG. 8 for use with a transducer array.

FIG. 7 shows an embodiment of the switches where each switch includes two large 50 v DMOS, two small 50 v DMOS, three 5 v inverters and 3 v latch and control logic. FIG. 8 shows the switch cell 35 in one embodiment with latch control. The state of each switch is stored in a latch. FIG. 9 shows an array of switch cells 35. Each switch cell 35 in the array 31 connects to column data lines, row latch lines, and a global strobe signal. Four data bits are latched at a time. The strobe signal transfers the latch data to the switch controller. Other state controls may be used.

The latch control is configured by loading input control data. Each column has eight data bits and an address decoder controlled by a load state machine. Each row has an address decoder that generates the two latch signals. Each hex cluster has a dedicated eight bit input data bus for a total of 7×8=56 data lines. Additionally, there are several global control signals.

In other embodiments, the switches 70, 72, and/or 74 for forming the electronically rotating aperture are semiconductor switches, other transistors, MEMS switches or other switches for electrically connecting or disconnecting elements 36 and/or system channels 33 of the beamformer 14. The same or different type of switch is used for the different switches. For example, the same type of switch (e.g., the switch shown in FIG. 6) is used, but the lateral switches 70 are of a different size than the vertical switches 72. Any now known or later developed switch may be used.

The switch is sized so that the switch layer 34 covers the area of the acoustic layer 30 without being substantially larger or smaller, but other sizes may be provided. "Substantially" accounts for manufacturing tolerance, extra area associated with entry switches, or a few wavelengths.

The switch layer 34 provides for routing one-dimensional array signals into and out of the two-dimensional switch cell matrix. The traces from the beamformer channels 33 or coaxial cables connect or are connectable with three different entry switches (e.g., one for each primary direction of the hexagonal arrangement), but may connect with more or fewer.

The macro elements 38 are formed by interconnecting lateral switches 70. One of the entry switches 74 connects with each of the macro elements 38. Some entry switches 74 are used to connect the macro elements 38 at the configured angle and other entry switches 74 are not used. The lateral switches 70 interconnect the switch cells 35 for the macro elements 38. The vertical switches 72 for each switch cell 35 connect one or more acoustic elements 36 to the switch cell 35, completing the interconnection of the beamformer channel 33 with the acoustic elements 36 in macro elements 38 for an aperture operating as a one-dimensional array. The other regions of the switch layer 34 operate in a similar manner to form the one-dimensional aperture.

Other layouts of switch cells 35, grids, and interconnections are possible. For example, the switch cells 35 operate differently to form the macro elements 38 at different angles. The same or different entry switches 74 are used depending on the angle of the macro elements 38. By using regions on the switch layer 34, the number of acoustic elements 36 and/or switch cells 35 used for a given macro element 38 may be limited, such as to fewer than ten (e.g., nine) or other number of serially connected high voltage lateral switches. By limiting the number of switches, the resistance requirements for the switches may be reduced, resulting in smaller sized switches. Greater numbers of switches may be used for a given macro element 38.

Referring again to FIG. 2, the spherical lens 32 is stacked above the switch layer 34 and the acoustic layer 30. In other embodiments, a lens with no focus, no lens, or another lens is provided. The lens 32 is an acoustic window. The spherical lens 32 assists with beam formation in concert with electronic rotation of a one-dimensional array since the spherical lens always focuses the sound in the direction perpendicular to the rotated row of elements, regardless of the rotation angle. The lens 32 provides elevation focus at a desired depth regardless of the angle of rotation of the one-dimensional aperture on the array 31.

The switch layer 34 is configured to form macro elements 38. In one embodiment, the configuration (e.g., selection of which switches are open and which are closed) is stored in a memory in the transducer probe 12. The memory may be programmable or read only. The memory stores different configurations (switch maps), each associated with a different one-dimensional aperture. For example, different configurations are provided for different angles of rotation, translations and/or depths of focus of the one-dimensional aperture. The different configurations may be indexed by rotation angle or merely a next increment command on a strobe. In other embodiments, the switch configuration is programmed, set, or controlled by the imaging system with or without a memory in the transducer probe 12.

The one-dimensional aperture is a one-dimensional array of one-dimensional array elements (i.e., macro elements 38). Due to the layout or connectability of the switches of the switch layer 34, the switches are configured to form the acoustic elements 36 into the one-dimensional array of macro elements 38. The acoustic elements 36 are connected together so that the same beamformer channel connects with the acoustic elements 36 of the same macro element 38. When connected, the switches are configured in the one-dimensional aperture.

The one-dimensional aperture of macro elements 38 may be used to scan a plane. Transmit and receive beams may be steered to various angles, such as +/−45 degrees (theta) with time delay focusing of the beamformer 14. Combined with rotation (phi) of the aperture, acoustic transmit and receive beam may be focused anywhere within the 90 degree cone extending out from the face of the acoustic layer 30. In the embodiment shown in FIG. 2, the 2500 element 2D acoustic layer 30 or matrix may be electronically configured into about 50 macro elements 38 as a 1D transducer or aperture with elements oriented at any rotational angle (phi). By resetting the switches, additional one-dimensional arrays are formed rotated relative to each other on the acoustic element layer 30. Each rotation is associated with at least one switch being set differently. For some rotations, the switches may be associated with the same or different connections of the lateral, vertical, and entry switches.

In one embodiment, the acoustic elements 36 of the acoustic layer 30 have a finer pitch than the switch cells 35 of the switch layer 34. This is in addition to or as an alternative to the aperiodic distribution of acoustic elements 36 in the acoustic layer 30. The difference in pitch between the switch cells 35 and the acoustic elements 36 is from a different general, average, or overall periodicity (i.e., different size grid). In one embodiment, the switch cells 35 have a more coarse $\lambda/2$ pitch to maximize the silicon area available to place high voltage switches. The corresponding grid (e.g., hexagonal, rectangular, or triangular periodicity grid) may maximize signal routing efficiency. The acoustic elements 36 have a finer pitch, such as $\lambda/2$ or less (e.g., $\lambda 3$, $\lambda/4$, or other). Since each switch cell 35 is connectable with a plurality of acoustic elements 36, the difference in pitch still provides for selection of most, if not all, of the acoustic elements 36. In other embodiments, the pitch is the same or the acoustic elements 36 have a more coarse pitch than the switch cells 35.

The difference in pitch allows formation of macro elements 38 having irregular variation. Macro elements 38 are formed with the switch layer 34 having a different pitch than the acoustic layer 30. The acoustic elements 36 also have randomized or partially randomized shifts. In other embodiments, the acoustic elements 36 do not have the randomized shifts. The difference in pitch allows for further randomization or otherwise more aperiodic macro elements 38.

The irregular variation is of the acoustic elements 36 in a given macro element 38, the edges of the macro element 38, and/or the steps of the macro element 38. By partially randomizing the acoustic elements 36 selected to be in a macro element 38, the periodic steps along the edge of the macro element 38 may be removed or reduced. The steps are performed in smaller increments and/or at different distances along the elevation length. For a given macro element 38, the steps are aperiodic or less periodic than for FIG. 8. Alternatively or additionally, the steps or periodicity across macro elements is different. The steps for a given macro element 38 occur at different distances along the elevation length and/or with a different periodicity than for adjacent macro elements 38.

The beamformer 14 is a transmit beamformer, receive beamformer, combinations thereof, or other now known or later developed device for scanning a region with the transducer probe 12. In one embodiment, the beamformer 14 includes transmitters or waveform generators for generating electrical waveforms for each element of a transmit aperture. The waveforms are associated with phase and amplitude. The waveforms for a given transmit event may have the same or different phasing. The electrical waveforms are relatively weighted and delayed to form an acoustic beam with a desired phase and amplitude characteristic. For example, the transmit beamformer includes amplifiers, phase rotators, and/or controllers to generate sequential, steered pulses with the desired phase and amplitude in relation to other acoustic beams. Converging, diverging or planar beams may be used.

The beamformer 14 may include receive beamformers, such as delays, phase rotators, amplifiers, and/or adders for relatively delaying and summing received signals to form one or more receive beams with dynamic focusing. For example, using shared processing, separate processing, or combinations thereof, a plurality (e.g., tens or hundreds) of parallel receive beamformers are provided to form a respective plurality of receive beams in response to a given transmit beam. Alternatively, the beamformer 14 includes a processor for Fourier or other analysis of received signals to generate samples representing different spatial locations of the scanned region.

The transducer probe 12 and beamformer 14 are connected together, such as the beamformer channels 33 connecting through coaxial cables to the transducer probe 12. The transducer probe 12 and beamformer 14 are configured to scan a planar region or a segment of a planar region. The beamformer 14 is controlled or programmed to perform the scan. The beamformer parameters, such as relative delays and/or phasing for focus, apodization, beam amplitude, beam phase, frequency, or others, are set. The aperture for transmit and the aperture for receive on the transducer probe 12 is set. The beamformer 14 and transducer probe 12 are used to generate the waveforms for the aperture and convert the waveforms to acoustic energy for transmitting the beam, and used to receive acoustic energy at the receive aperture, convert the acoustic energy to electrical energy, and beamform the received electrical signals.

Electric steering may be used to scan a volume and/or plane. A volume scan may be performed using any pattern or distribution of scan lines and/or apertures. In one embodiment, an acquisition scan plane is positioned within a three-dimensional region by setting a one-dimensional aperture. Acoustic energy is transmitted in any of various now known or later developed scan patterns along the scan plane for acquiring data. The scan plane is then altered to another location in the volume by setting a different aperture.

For a given volume, the scans may be repeated. By repeating the scans, a sequence of frames of voxel data is obtained. Each frame represents the entire three-dimensional scanned volume, but may only represent smaller regions within the volume, such as a plane. By repeating the scanning, a plurality of frames of beamformed data representing the volume and/or plane within a given cycle is acquired. Any of scan line, part of frame, frame, or group of frame interleaving may be used.

The beamformer 14 may be configured, using the switches in the system, switches of the transducer probe 12, beamformer channel selection, combinations thereof, and/or other configuration approaches to interleave two or more moving apertures on the array. The configuration is performed using hardware, software, or combinations thereof. The two moving apertures move in different directions such that adjacent locations for the moving apertures are separated by five or fewer scans using other aperture locations of the moving apertures. For example, the moving apertures use two or four one-dimensional apertures. The different directions are counter rotation relative to the two-dimensional array for rotation. The beamformer 14 is configured to scan different planes for the different locations of the moving apertures. Alternatively, the different directions are counter translations, such as counter translation around a ring array where each aperture location is for scanning a different segment in a plane. Other rotation patterns for the scan planes may be used.

For each aperture position, the beamformer 14 is configured to scan with any scan line format. In one embodiment, the scan line density changes as a function of origin, angle, aperture location, or both. For example, less scan line density occurs along a plane for scan lines in the center. Different aperture locations may scan with different densities in different locations.

The interpolator 20 is part of the beamformer 14, the detector 18, or separate. The interpolator 20 is a memory, buffer, phase rotator, processor, adder, multipliers or other components for interpolating in-phase and quadrature or other signals with phase information. The interpolator 20 is configured as hardware, with software or combinations thereof to interpolate at least some of the data output by the beamformer 14. For example, one or more samples representing scan lines between received scan lines are interpolated. As another example, data for a scan line is replaced by interpolated data. The interpolated data is output to the detector 18. The detector 18 operates on interpolated data, actual received data, or combinations of both. In alternative embodiments, the interpolator 20 is not provided.

The detector 18 is configured to detect data output by the beamformer 14 and responsive to the moving apertures. The detector 18 is an ultrasound detector. The detector is configured by hardware and/or software to detect from the beamformed and/or interpolated data. Any detection may be used, such as B-mode, Doppler or color flow mode, harmonic mode, or other now known or later developed modes. B-mode and some harmonic modes use single pulse scan techniques for detection. The intensity of the received signals in the frequency band of interest is calculated. Multiple pulse techniques, such as flow mode estimation of velocity or energy, may be used.

The detector 18 detects the response to the transmit beams for the scan of the volume. The spatial and/or temporal resolution of the detected data is based on the beamforming or scanning resolution. Detected data representing the volume is provided. Such frames of data are provided for the same or similar volumes (e.g., similar accounts for unintended transducer and/or patient movement offsetting the volume) at different times throughout a heart cycle, over time, or merely once.

The processor 16 is a rendering processor configured by hardware and/or software. The processor 16 is a general processor, control processor, application-specific integrated circuit, field-programmable gate array, graphics processing unit, digital circuit, analog circuit, digital signal processor, combinations thereof, or other now known or later developed device for generating a three-dimensional rendering of a volume scanned with different planes. The processor 16 is a single device or group of devices. For example, the processor 16 includes separate processors operating in parallel or sequence. As another example, the processor 16 includes a network of devices for distributed processing in parallel or sequence. In one embodiment, the processor 16 is a specific device for three-dimensional image rendering, such as a graphics processing unit, graphics card, or other device for rendering.

The processor 16 uses surface rendering, projection rendering, alpha blending, texturing or other now known or later developed rendering. The data may be resampled to a regular voxel grid. Alternatively, the rendering is performed from data in a scan format, such as associated with the actual scan lines and/or interpolated scan lines. In yet other embodiments, the processor 16 is not provided or is a scan converter for generating a two-dimensional image representing a scanned plane or a reconstruction of a plane from a scanned volume.

The processor 16, the detector 18, or a separate processor generates images from the volume scan and/or plane scan or other data output from the detector 18. For example, grayscale and/or color coding is used to generate a B-mode, Doppler mode, or B-mode Doppler mode combination. Any image, such as a three-dimensional rendering, is output to the display 24.

The display 24 is a CRT, LCD, plasma, projector, printer, or other now known or later display device. The display 24 receives the image data from the processor 16 or other component and generates the image. A perfusion map, three-dimensional rendering, two-dimensional image, or other image is displayed. For example, a perfusion map is generated as a function of the detected contrast agents, such as modulating pixels by the perfusion rate for locations representing the tissue.

The memory 22 is a tangible (non-transitory) computer readable storage medium, such as a cache, buffer, register, RAM, removable media, hard drive, optical storage device, or other computer readable storage media. The memory 22 is tangible by not being a signal, but a device. Computer readable storage media include various types of volatile and non-volatile storage media. The memory 22 is part of the imager 17, the imaging system 16, the transducer probe 12, or separate from both. The memory 22 is accessible by the processor 16 or switches of the transducer probe 12.

In one embodiment, the memory 22 stores switch configuration data. The memory 22 may store data for use by the processor 16, such as storing detected and/or image data. Additionally or alternatively, the memory 22 stores data representing instructions executable by the programmed processor 16 for scanning with ultrasound and/or controlling the switches of the transducer probe 12. The instructions for implementing the processes, methods and/or techniques discussed herein are provided on computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 10:
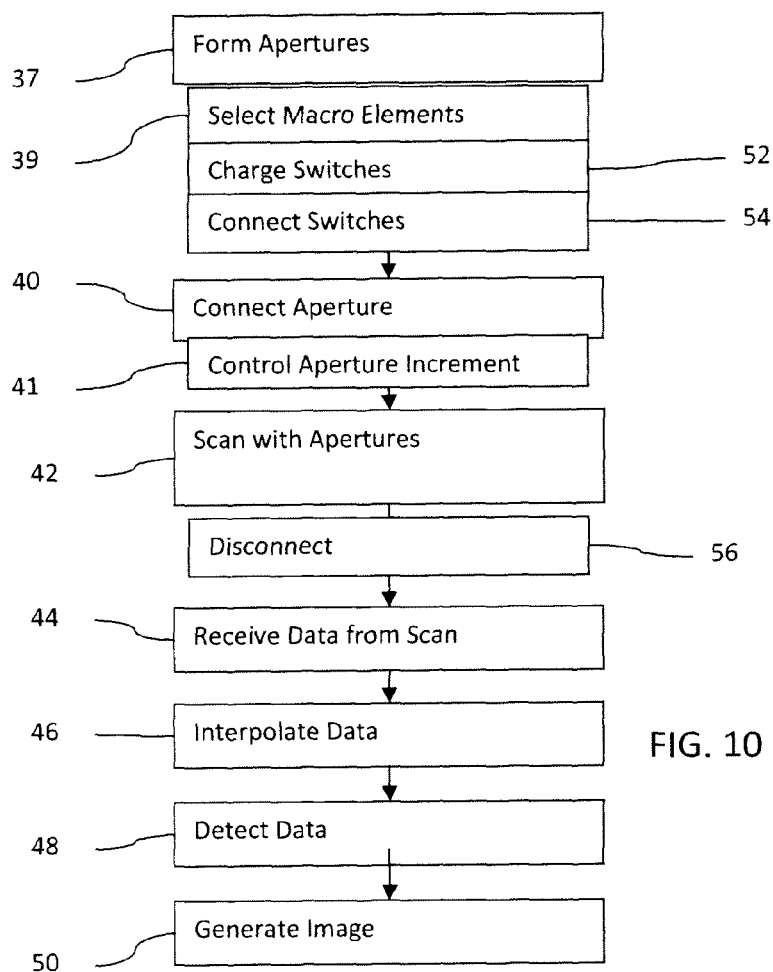
FIG. 10 is a flow chart diagram of one embodiment of a method for scanning with ultrasound.

FIG. 10 shows a method for operating a two-dimensional transducer array in medical diagnostic ultrasound imaging. The method includes acts for connecting elements together in medical diagnostic ultrasound imaging. In one example embodiment, scanning of a three-dimensional volume is provided using different element interconnections. In other embodiments, the scanning is of a plane using a given aperture established by interconnection of elements. The method is implemented using the system of FIG. 1, the transducer probe 12 of FIG. 2, or a different system. The method is performed in the order shown or a different order. Additional, different, or fewer acts may be provided. For example, acts 42, 44, 46, 48, and/or 50 are not provided or provided in non-real time. As another example, acts 37, 39, 54 and 56 are performed with or without other acts.

In act 37, a plurality of different apertures is formed in a multi-dimensional array of transducers. The apertures are formed by switching in acts 54 and 56, such as one or more switches for each element connecting the elements together and/or to beamformer channels. For example, the switching and arrays described in U.S. Pat. No. 6,676,602, the disclosure of which is incorporated herein by reference, is used. As another example using the switching layer 34 and acoustic layer 30 discussed above, beamformer channels 33 are connected to elements by two layers of switches, one layer having a channel matrix interconnected laterally and another layer having an acoustic element matrix interconnected to the channel matrix along another direction. Alternatively, one or more beamformer channels 33 are turned on or off to include or not include a connected element in the aperture. Other aperture selections may be used.

Each aperture includes one or more transducers. For example, the apertures are one-dimensional. The aperture is formed from a plurality of transducers along a straight or curved line. In other embodiments, the apertures are multi-dimensional, such as having a 1.25D, 1.5D, or 1.75D arrangement of two or more rows of elements.

The switches or beamformer operation forming the aperture at a given time are configured to switch quickly, allowing real-time aperture change or operation free of mechanical movement. Electronic switching may occur more rapidly than mechanical movement. Any type of switch may be used for electronic movement of the aperture.

Each aperture is at a different position on an array. The aperture may slide along an array. For example, the aperture is translated laterally or in azimuth along an array of elements. As another example, the aperture rotates across the face of a multi-dimensional array. The rotation is about a center or other location on the multi-dimensional array, but may be about a point spaced from the face of the array. Each aperture is rotated by a different amount. In another example, the aperture translates laterally in elevation across a multi-dimensional array. Combinations of translation and rotation may be used. Each translated or rotated location corresponds to another aperture. The apertures in sequence correspond to a given aperture being translated or rotated to the different locations.

Any step size for the translation and/or rotation may be used. The step size is the same between each aperture location. For example, equal amounts of rotation are provided for each aperture location. In alternative embodiments, the step size for rotation and/or translation may vary, such as having a smaller step size to more heavily sample one region over another or to reduce frame rate by providing lesser sampling for some regions. Each of the different one-dimensional apertures corresponds to a different aperture rotation angle or position relative to the multidimensional array.

The transducers are in a hexagonal, rectangular, triangular, or other grid. Given the different positions of the one-dimensional apertures on the array, one or more of the apertures may have elements at a non-primary or non-natural angle to the grid, causing the elements to be other than along a straight line of the transducers. For example, a hexagonal grid has three primary axes along which a straight line of transducers may be connected. For other angles, the elements have jogs or steps to conform to the desired line.

For scanning, the different apertures correspond to different scan line positions. For example, the aperture is a one-dimensional aperture used to scan a plane. Scan lines in a sector, Vector™, linear or other format are used for scanning at the aperture location. The format is repeated at other aperture locations for other scan lines in the continuous region.

In act 39, the apertures of act 37 are formed by selecting transducers. The selected transducers (acoustic elements) are for forming a plurality of different elements of the one-dimensional array of the aperture. Substantially parallel groups of the transducers are selected for elements of the one-dimensional apertures. "Substantially" accounts for the shifts in the transducers and/or for aperiodic formation. The selected transducers in the groups are selected to be aperiodic along an elevation length of the corresponding elements. Any level of aperiodic may be provided, such as aperiodic in a range of frequencies at a bandwidth of operation of the array. Aperiodic elements have an irregular edge for each of the elements. The irregular edge is formed from connected adjacent transducers such that an azimuth width of the elements varies along the elevation length without periodic steps along the length of the element or at least half of the length of the element. For other elements, such as elements for angles along the primary direction of the grid, periodic distribution may be provided. The period of these elements has sufficiently high frequency to cause less side lobe at the imaging frequencies. Macro elements with periodic patterns of the transducers may be used in other embodiments.

The selection is performed with switches. The switches may have any arrangement. In one embodiment, the switches are grouped such that switch groups have a greater pitch than the transducers. The switch groups are sized to have an about one-half or less pitch of a center frequency of operation of the one-dimensional apertures. In one embodiment, the transducers are a first layer of microelectromechanical devices, and the switch groups are a second layer. The layers are stacked along a depth dimension. The switch groups include at least one switch configured to selectively connect with an adjacent switch group and at least two switches configured to selectively connect with respective transducers. In other embodiments, the switches are provided without groupings, such as one switch for each transducer element and other switches to connect elements together.

In additional or alternative embodiments, randomization or shifting of the transducers relative to each other is fixed or part of the layout (manufacture or design) of the transducer array. This introduces an irregular shape or pattern along the elements of the selected one-dimensional array.

In one embodiment for forming the aperture, the switches are charged in act 52. For a given aperture configuration, a plurality of switches are to be turned on or form a connection. Prior to or in preparation for connecting, the switches may be charged. For example, the gate of a transistor for passing ultrasound signals is charged. Current is allowed to flow in order to charge the parasitic capacitance to ground across the transistor. The charging allows the gate, when disconnected, to maintain the pass transistor in an on state.

The switch may be charged in any manner. In one embodiment, similar, non-ground voltages are applied to both the source and the gate of a control transistor with a drain connected to the gate of the pass transistor. The voltage, such as a 3-4 volt pulse, allows current to pass through the body diode of the control transistor. This current charges the parasitic capacitance of the pass transistor.

While being charged, the pass transistor is prevented from connecting. Any prevention may be used, such as not connecting an upstream or downstream transistor. In one embodiment, a source or drain of the pass transistor is connected to ground by another control transistor during the charging.

In act 54, the switches for forming the aperture are connected. After any charging, the switches are turned on (closed) to connect transducers to each other, to connect transducers to switches, to connect transducers to beamformer channels, to connect switches to switches, and/or to connect switches to beamformer channels. For example, a switch connects one transducer to another transducer. The connection is formed with a single switch or through a plurality of switches (e.g., one switch connecting the transducer to a path, another switch connecting the path to yet another switch and that other switch connecting the path to the other transducer).

In one embodiment, a gate of the switch forming the connection floats while "on." For example, a control transistor disconnects the gate. By maintaining the control transistor off (e.g., similar voltages to the gate and source of the control transistor), the gate is disconnected. Where multiple pass transistors are provided with a common gate connection, the multiple gates are disconnected from ground or a source, allowing the gates to float. To go from the transition to "on," the other control transistor disconnects the source or drain of the switch (e.g., pass transistors) from ground. Other operations to turn on the switch may be provided.

For connecting the switches in act 54 to form the apertures of act 37, the switches are controlled. Any control may be provided, such as data transfer of the switch settings. In one embodiment, the control is provided by incrementing through a table of switch configurations. Switch control data is stored off chip in a field programmable gate array (FPGA) or other memory. The switch control data is a group of pre-calculated switch maps. Global control signals include clock, row/column, and load. The row/column designates a particular switch map or map memory location. The load control allows for loading the next switch map into the latches controlling the switches. A state machine controls the column and row address counters and generates latch signals for each switch. Other control approaches may be used.

Data transfer starts with load going active. The first data byte is latched into the first column bits, the column address increments, and data is latched into the columns till the row/column signal asserts. At this point, the state machine multiplexes the LSB bits into the data lines and generates the row address and lsb latch signals. Then, the state machine multiplexes the MSB bits and an msb latch signals. After those two clock cycles, the data transfer commences. The control scheme starts from column zero and row zero. The number of column and rows is a function of the row/column and the load signal. Other control and data transfers may be used.

In act 40, the one-dimensional apertures are connected with an ultrasound system for use as one-dimensional arrays. The connection is performed by switches, such as connecting beamformer channels through coaxial cables with entry switches adjacent to the array or aperture and spaced from the system. The connection is the same or different as in acts 52 and 54. Separate channel connection (entry) switches are used, but other switches, such as edge switches or switches also used to interconnect elements, may be used. Another example connection is of the transducer assembly to the ultrasound system. This connection allows signal to pass between the imaging system and the transducer probe. The beamformer may be all in the imaging system, all in the transducer probe, or partially in the transducer probe and partially in the imaging system (partial beamformation in the probe).

In act 41, the connections of the channels with the array are controlled. The selection of the different one-dimensional apertures is controlled. The configuration of switches to form the aperture is loaded from the imaging system to the transducer probe. Alternatively, the configurations are preloaded in a programmable memory or a read only memory.

The connections may be controlled through indication of a specific aperture to use. In other embodiments, the connections are controlled by sequencing through a programmed or predetermined sequence of apertures. Based on an increment command, the next aperture in the sequence is selected. A signal on a single control line may indicate rotational or translation increment. A memory adjacent the multi-dimensional array and spaced from the ultrasound system controls the selecting in response to the rotational increment command provided by the ultrasound system.

Any sequence of apertures may be used. In one embodiment, an interleaved sequence of the different apertures is used for scanning. Two or more apertures are moved during the scanning. The aperture locations are grouped into two or more sets, each set providing the locations of apertures making up a given aperture movement. The scanning is interleaved between the sets, such as forming an aperture at one location for set 1, then forming an aperture at another location for set 2, then forming yet another location for set 1, and so on. Multiple apertures may be scanned from a given set before interleaving or switching to the apertures of another set. The order of the apertures within each set is arranged to reduce or minimize the amount of time between scanning adjacent portions of the scan region.

In act 42, the apertures are used for scanning. The electrically common, interconnected elements (macro elements) are used for imaging. One or more scan lines are formed for each aperture location or aperture. In the embodiment with a one-dimensional array for each aperture, a plurality (e.g., tens or hundreds) of scan lines are scanned.

Scanning is performed by beamformation. Relative delays and/or apodization determine the scan line origin and angle. For a one-dimensional array, the angle is an azimuth angle relative to the aperture. Waveforms are applied to respective macro elements to form a transmit beam. The waveforms pass through the connected switches to the transducer elements. The waveforms are unipolar pulses, but may be bipolar pulses in other embodiments. For receive operation, the electrical signals representing echoes pass through the switches to the beamformer channels.

Acoustic energy is transmitted along the scan line. Receive beamformation samples the echoes from the transmitted acoustic energy along the same or a different scan line. In one embodiment, one scan line is used for each transmit and receive event. In another embodiment, the transmitted acoustic energy has a beam width in azimuth for receiving along two or more scan lines simultaneously or in response to the same transmitted beam. For example, eight receive beams are formed for each transmit beam. A fewer or larger number of receive beams may be formed for a given transmit event.

By scanning with a plurality apertures at different locations, a volume is scanned in one embodiment. A planar scan is provided in another embodiment, such as with the ring array. By scanning along a plurality of scan lines in a sequence, the continuous region may be sampled.

For the volume scan, the three-dimensional volume is scanned with ultrasound sequentially from the different one-dimensional or other apertures at different rotation angles and/or translations. In one embodiment, each aperture is used for scanning a plane. A two-dimensional beamformer may be used to sequentially scan a volume without the need for additional beamformer channels. For example, seven transmit events are performed for each plane or aperture. The transmit events have about 13 degree spacing to collect information for an about 90 degree sector or Vector™ scan for a given rotation angle slice. Multibeam receive samples the receive beam using 8-beams spaced about 1.6 degrees apart for each transmit beam. Combined, a scan of a planar slice uses 56 receive lines. Using sixty rotation angle slices or apertures spaced about 3 degrees apart, the contiguous volume region is scanned. The receive samples are combined into a data set or collected to sample the complete space over a full 180 degree rotation space. Sixty rotation angle slices by 7 transmit events requires 420 transmit events. If the depth to be sampled is about 150 mm, requiring about 200 μsec of round trip sound transit time, the volume sampling rate is about 12 Hz. This rate provides for visually acceptable real-time imaging while scanning. One example is given above. Different numbers of receive beams per transmit beam, number of transmit beams per plane or aperture, number of apertures, depths, or other values may be used.

The frame rate may be improved by reducing the lateral sampling density for angles near the center of the scan region as compared to the scan line density away from the center. The distribution of scan lines in the volume may be made more even, such that the density is similar at the center as at the edges of the volume. Other distributions may be provided by varying the scan line density azimuthally for each aperture location. The same variation in scan line density is used for each aperture location.

In act 56, the transducers forming macro elements are disconnected. As each new aperture is formed or as the macro elements change due to different focal locations of scan planes, the switches are disconnected. All the switches are disconnected or turned off. Alternatively, only the switches to be in a different state for the next switch map are disconnected. Where a given switch is connected in a current map and will be connected in the next map, the switch is maintained in the on or connected state. After disconnection, acts 52 and 54 may be repeated for the next aperture or macro element configuration.

The switches disconnect the transducers from each other by disconnecting (opening) one or more of the switches. For example, the gate of the switch or pass transistors is connected to ground, turning off the pass transistors. Alternatively or additionally, the source or drain of the pass transistors is connected to ground. Other controls for opening the switch may be provided.

In act 44, data is received for the receive scan lines. The data is received by beamformation. Echoes impinging on the elements of the current aperture are transduced to electrical energy. The electrical energy from each element of the aperture is relatively delayed and/or weighted to beamform for a given location along each scan line. Digital and/or analog dynamic beamforming may be provided. The samples may be filtered or otherwise combined, such as for imaging at a cubic fundamental or phase inversion imaging. Any now known or later developed reception and formation of samples representing locations along one or more scan lines for each transmit event may be used.

By receiving data for each aperture, the planar or volume region is scanned. The data representing different locations within the region are provided.

In act 48, the received data and/or the interpolated data are detected. Any detection process may be used. For example, the intensity of the return is detected as B-mode data. As another example, the energy (power), velocity, and/or variance of moving tissue or fluid are detected as Doppler data. Contrast agent, harmonic, or other types of detection may be provided.

Some types of detection use a plurality of samples for each spatial location. The scanning of act 42 for a given aperture location is performed multiple times to acquire the data for the detection. The repetition is performed before scanning with a different aperture and/or for a different scan line. Alternatively, the sampling for detection may be interleaved with other scans.

In act 46, an image is generated from the detected data. The data received by scanning is used to generate the image. The image represents a volume, plane or line. For two-dimensional imaging, the data may be scan converted and mapped to display values. For example, B-mode information is mapped to a gray scale and Doppler data is mapped to a color scale.

For a volume, the image is rendered from the data representing the volume. Any now known or later developed rendering may be used. For example, surface rendering or projection rendering are performed. The image is rendered as a three-dimensional representation from data for the various scan planes. Alternatively, the data from the scan planes is interpolated to a regular grid, and the image is rendered from the grid data. Shading and/or opacity weighting may be used. The data may be filtered before or after image generation.

The generation of the image occurs in real-time with the scanning. For example, the image is generated while still scanning to acquire data for subsequent images. The image is generated in a same imaging session as the acquisition. The processing delay between scanning and generating the image may be a few seconds or less, such as less than one second. The volume is scanned a plurality of times each second. The images are generated at the scan rate in a short time to allow processing after completion of corresponding scans of the entire volume. In other embodiments, the data is stored. The image generation occurs from the stored data rather than being in real-time with the scanning.

While the invention has been described above by reference to various embodiments, it should be understood that many changes and modifications can be made without departing from the scope of the invention. The above embodiments are examples. It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A transducer array for medical diagnostic ultrasound imaging, the transducer array comprising:
   a plurality of elements;
   a plurality of channel lines connectable with a beamformer; and a plurality of switches arranged to interconnect sub-sets of the elements together into macro elements and to interconnect the macro elements with respective channel lines based on a direction of an acoustic aperture of the elements;

wherein at least a first one of the switches comprises at least two pass transistors having gates and sources and a controller arranged to float the gates of the at least two pass transistors when the at least first one of the switches is on, and wherein the at least first one of the switches has a first configuration where the switch is on, a second configuration where the at least first one of the switches is off, and a third configuration where the at least first one of the switches is transitioning to on, the transitioning to on configuration having a different combination of connections with the gates and the sources than the first and second configuration, the different combination of connections including a connection to ground so that the at least first one of the switches does not pass signal during the transitioning to on configuration and including disconnecting from the ground during the on configuration, the transitioning to on configuration including disconnecting an input of the at least first one of the switches from an output of the switch.

2. The transducer array of claim 1 wherein the at least two pass transistors comprise Metal Oxide Field Effect Transistor (MOSFET).

3. The transducer array of claim 1 wherein the one switch is a bi-directional high-voltage switch.

4. The transducer array of claim 1 wherein a first of the at least two pass transistors has a drain connected to one of the elements or a second one of the switches, the first pass transistor having a gate connected with a gate of a second of the at least two pass transistors, a source of the first pass transistor connected with a source of the second pass transistor, and a drain of the second pass transistor connected with a first one of the channel lines or a third one of the switches.

5. The transducer array of claim 1 wherein the controller comprises at least two control transistors.

6. The transducer array of claim 5 wherein a first of the control transistors has a drain connected with gates of the at least two pass transistors, a gate connected with a first control signal, and a source connected with a second control signal.

7. The transducer array of claim 5 wherein a second of the control transistors has a drain connected with sources of the at least two pass transistors, a source connected with the ground, and a gate connected with a third control signal.

8. The transducer array of claim 7 wherein a first of the at least two pass transistors has a drain connected to one of the elements or a second one of the switches, the first pass transistor having a gate connected with a gate of a second of the at least two pass transistors, the source of the first pass transistor connected with the source of the second pass transistor, a drain of the second pass transistor connected with a first one of the channel lines or a third one of the switches, wherein a first of the control transistors has a drain connected with the gates of the first and second pass transistors, a gate of the first control transistor connected with a first control signal, and a source connected with a second control signal.

9. The transducer array of claim 1 wherein the controller connects the gates and sources of the at least two pass transistors to ground for the switch to be off, the controller charges the gates during the transition to on while maintaining the sources at the ground, and the controller disconnects the sources from the ground for the switch to be on.

10. The transducer array of claim 1 wherein the plurality of switches are configured to interconnect different sub-sets of elements into different macro-elements multiple times within a second, wherein the first one of the switches has a higher on resistance than a second one of the switches.

11. A first switch for interconnecting elements of an electronically configurable transducer array in medical diagnostic imaging, the first switch comprising:
a first connection with a second switch or a first beamformer channel;
a second connection with a third switch or a first transducer;
a first MOSFET having a gate, a source and a drain;
a first control transistor connected with the gate,
wherein the first switch has a first configuration where the switch is on, a second configuration where the first switch is off, and a third configuration where the first switch is transitioning to on, each of the first, second and third configurations having different source, gate, and drain combination of connections, the different combination of connections including a connection to ground so that the first switch does not pass electrical signals during the transitioning to on configuration and including disconnecting from the ground during the on configuration, the transitioning to on configuration including disconnecting an input of the first switch from an output of the switch, and
wherein the first control transistor is operable to float the gate when the first MOSFET is on where the electrical signals for beamformation pass through the first switch when the first MOSFET is on and do not pass through when the first MOSFET is off.

12. The first switch of claim 11 wherein the electrical signals are unipolar.

13. The first switch of claim 11 wherein the first control transistor has a drain connected with the gate of the first MOSFET, the first control transistor allowing the gate of the first MOSFET to float by having a common voltage applied at the gate and source of the control transistor and having the ground connected to the source of the control transistor for the MOSFET to be off.

14. The first switch of claim 11 further comprising a second control transistor connected with a source of the first MOSFET, wherein, during the transition to on, the second control transistor connects the source of the first MOSFET to the ground while the first control transistor charges the gate of the first MOSFET through a body diode by having a common voltage applied to the gate and source of the first control transistor.

15. The first switch of claim 11 further comprising a second MOSFET where the sources of the first and second MOSFETs connect together, a drain of the first MOSFET comprising the first connection and a drain of the second MOSFET comprising the second connection.

16. A method for connecting elements together in medical diagnostic ultrasound imaging, the method comprising:
charging, with a switch in a state disconnecting an input of the switch from an output of the switch, a gate of the switch prior to connecting;
connecting, with the switch, a first transducer element to a second transducer element, the gate of the switch disconnected during the connection of the first and second transducer elements;
imaging with the first and second transducer elements as an electrically common macro element during the connecting; and disconnecting the first transducer element from the second transducer element with the switch, the gate of the switch connected to ground during the disconnecting.

17. The method of claim 16 wherein connecting is established by a control on the source or drain of the switch.

18. The method of claim 16 wherein imaging comprises imaging with unipolar pulses passed through the switch, wherein the switch has a higher on resistance than an additional switch, both switches passing the unipolar pulses.

19. The method of claim 16 wherein the switch is bi-directional and comprises first and second MOSFETS, connecting comprising turning both the first and second MOSFETs on with the gate being a common connection to both gates of the first and second MOSFETs.

20. The method of claim 16 wherein connecting comprises disconnecting the source or drain of the switch from the ground and wherein disconnecting comprises connecting the gate to the ground and connecting the source or the drain to the ground.

* * * * *